United States Patent [19]
De Luca et al.

[11] 4,350,762
[45] Sep. 21, 1982

[54] AMINOPYRINE IMPROVED TRINDER'S REAGENT AND DOSING PROCESS FOR HYDROGEN PEROXIDE FROM ENZYMATIC OXIDATION OF METABOLIC SUBSTRATA WITH THE SAME

[75] Inventors: Ugo De Luca, Milan; Francesco Zoppi, Treviglio, both of Italy

[73] Assignee: ELVI S.p.A., Milan, Italy

[21] Appl. No.: 231,152

[22] Filed: Feb. 3, 1981

[30] Foreign Application Priority Data

Feb. 4, 1980 [IT] Italy .................... 19672 A/80

[51] Int. Cl.³ .................................... C12Q 1/62
[52] U.S. Cl. ........................... 435/10; 23/230 B; 23/909; 23/925; 252/408; 435/11; 435/14; 435/15; 435/18; 435/19; 435/20; 435/25; 435/26; 435/28
[58] Field of Search ............... 435/10, 11, 14, 15, 435/18, 19, 20, 25, 26, 28; 23/230 B, 909, 925; 252/408

[56] References Cited

U.S. PATENT DOCUMENTS

Re. 29,498 12/1977 Meiattini .................. 435/25 X
4,226,713 10/1980 Goldberg .................. 435/11 X
4,247,631 1/1981 Nix et al. .................. 435/11 X
4,251,629 2/1981 Yamanisi et al. .......... 435/10 X
4,291,121 9/1981 Acquati et al. ............ 435/10
4,295,853 10/1981 Kasahara et al. .......... 435/11 X

FOREIGN PATENT DOCUMENTS 2738135 1/3/79 Fed. Rep. of Germany
7712266 4/7/77 Netherlands

OTHER PUBLICATIONS

"Chemical Abstracts", vol. 90, no. 5, Jan. 29, 1979, p. 217, no. 3581h, by P.V. Sundaram et al.: "Immobilized-enzyme nylon-tube reactor for routine determination of uric-acid in serum".

"Chemical Abstracts", vol. 90, no. 19, May 7, 1979, p. 254, no. 147965k, by P. Fossati et al.: "Emerson-Trinder reaction, study of various chromogens and analyses of main interferences".

Romps Chemie-Lekikon vol. 8 pages 174 and 167.

Primary Examiner—Robert J. Warden
Attorney, Agent, or Firm—Young & Thompson

[57] ABSTRACT

An aminopyrine-improved Trinder's reagent is disclosed to be used for the dosing of hydrogen peroxide from enzymatic oxidation of metabolic substrata, such as glucose, cholesterol, uric acid, tryglycerides and coline. The use of such an improved reagent in Trinder's reaction enables to avoid any interference from bilirubin, particularly in the determination of uric acid. The dosing process (for uric acid) is also disclosed by means of such a reagent.

3 Claims, No Drawings

AMINOPYRINE IMPROVED TRINDER'S REAGENT AND DOSING PROCESS FOR HYDROGEN PEROXIDE FROM ENZYMATIC OXIDATION OF METABOLIC SUBSTRATA WITH THE SAME

This invention relates to a Trinder's reagent improved with aminopyrine (4-dimethylamino-2,3-dimethyl-1-phenyl-3 pyrazoli pyrazolin-5-on) and a metering method for hydrogen peroxide, by enzymatic oxidation, from specific metabolic built substrata, through the use of such an improved Trinder's reagent.

Trinder's reaction (Ann. Clin. Biochem. 6,24 (1969) is widely used in clinical chemistry for the quantitative determination of the hydrogen peroxide formed from specific substrata through the action of several oxidases (glucosoxidase, cholesteroloxidase, uricase, α-glicerophosphatoxidase, colineoxidase). Substantially, it constitutes the detecting system, coupled with the enzimatic oxidizing reaction, of the diagnostically very important biological metabolites, such as glucose, cholesterol, uric acid and triglycerides.

Particularly, the known Trinder's chromogen system, comprising phenol and 4-aminophenazone (4-amino-1,5-dimethyl-2-phenylpyrazolone) is oxidized, in the presence of peroxidase, by hydrogen peroxide and produces a red chinonimminic compound, the colour strength of which provides an indirect measurement of the amount of metabolite (glucose, cholesterol, uric acid, present in the sample under examination.

However, Trinder's reaction is subject to the interfering action of substances of endogenous origin (bilirubin, hemoglobin) and exogenous origin (drugs).

Particularly bilirubin, the product of catabolism of "heme" (iron-protoporphirine), is a source of sure interference, because of being an alternate substratum for the oxidative system hydrogen peroxide/peroxidase (see Jacobsen, J., and Wennberg, R. P., Clin. Chem. 20, 783 (1974)) and is always present, in concentrations ranging from 0.6 to 1.2 mg/dl in normal human serums, and 3.0 to 30 mg/dl in hyperbilirubinemic human serums.

Such an interference from bilirubin in the "Trinder" type of chromogen systems was studied by Fossati, L. Principe Quad. Sclavo Diagn. 14,164 (1978) and Witte, D. L., Brown, L. F. and al., Clin. Chem. 24, 1778 (1978) who have suggested various solutions to obviate it.

The bilirubin interference is particularly sensible in the dosing by Trinder's method of uric acid in serum, where the concentration of such a metabolite is particularly low (2.7–7.5 mg/dl), that is more than ten times lower than that of glucose, which can also be dosed by Trinder's reaction.

This means that if absorptions are obtained at 500 nm for glucose, with a dilution ratio serum/reagent of 1:150, which absorptions are surely valid for the photometrical routine reading, it would be necessary to use dilution ratios serum: reagent of 1:15 in order to provide the same values of absorption and accordingly the same sensitivity the dosing of uric acid with "Trinder's reagent". However, under these conditions, the interference from bilirubin becomes determining so as to inhibit an exact quantification of uric acid, unlike the case of glucose determination, where the interference from bilirubin is negligible owing to the high dilution ratio of serum.

In order to obviate such a serious disadvantage, Barham D. and Trinder P. (Analyst 97, 142 (1972)) proposed to replace the phenol with 2-4 dichlorophenol sulphonate. Thus, they obtained a chromophore which was four times more intense than normal Trinder's reagent; that enabled them to reach a dilution ratio serum/reagent of 1:40, and thereby a reduction, but not an elimination of interference from bilirubin.

Afterwards, various methods were proposed to eliminate the interference from bilirubin, namely particularly:

(a) the sample dialysis with removal of the proteins and bilirubin (Klose, S., Stolz, M., Munz, E. and al., Clin. Chem. 24, 250 (1978)); however, this system suffers from the disadvantage of being applicable only to continuous flow analysers having a suitable dialysis unit;

(b) the oxidation of the bilirubin to biliverdin either with potassium ferricyanide (Prencipe, L., Fossati, P. and al., Quad. Sclavo Diagn. 14, 383 (1978)), or with ethylene peroxide/peroxidase (Peracino, N., Zoppi, F. and al., Uric acid assay: methods using uricase peroxidase-chromogen and uricase-catalasealdehyde dehydrogenase-NAD+, Clin. Enz. Symp., 2, pp. 245–258, 1979)).

However, this system suffers from the disadvantage of requiring a blank test for each of the samples to be analyzed, due to the low dilution ratio serum/reagent.

Further studies, intended to make the analytic method less cumbersome, and to overcome the above mentioned disadvantages, were directed to the direct determination of the various metabolites, particularly uric acid.

Thus, it was proposed:

(c) to oxidize the ferrocyanide to ferricyanide by the hydrogen peroxide/peroxidase system, thus blocking the interference action of bilirubin.

In the course of studies on the matter, it has now been found that, according to the present invention, the interference from bilirubin in Trinder's reaction can be eliminated in a high degree, when particularly it is applied to the analysis of uric acid by modifying the Trinder's reagent by means of the introduction of aminopyrine at high concentration in addition to the various constituents provided for the enzymatic dosing of uric acid with Trinder's modified chromogen system. In fact, it has been experimentally verified that the presence of aminopyrine at a high concentration with respect to that of 4-amino-phenazone, bilirubin and hydrogen peroxide, plays a basic role since it prevents the reaction between hydrogen peroxide, formed in the oxidation of uric acid (as a substratum) through the enzyme uricase, and bilirubin (free and conjugated), by mass action on the balance of Trinder's reaction. This is because aminopyrine takes part directly in Trinder's reaction forming with 2,4-dichlorophenyl sulphonate and hydrogen peroxide, a chromophore which has a colour only slightly less deep that that appearing in the reaction between 4-aminophenazone, 2,4-dichlorophenol sulphonate and hydrogen peroxide. This is due to the fact that all the hydrogen peroxide, when forming, is completely engaged by Trinder's system with aminopyrine and 4-aminophenazone, so that the interfering action of bilirubin is fully blocked.

Particularly, as far as aminopyrine concentration is concerned, it has been experimentally found that an effective concentration of the same is in the range of 1 to 30 g/l, preferably about 15 g/l.

Moreover, it has been found, in the experimental research for practically performing the uric acid assay in biological samples (serum or the like) with Trinder's reagent modified, by the addition of aminopyrine, according to the present invention, that the necessary condition for the realization of this new method is that the catalytic activities of the enzymes and concentrations of the various components taking part in the reaction are maintained at the following optimum levels:

| | |
|---|---|
| Peroxidase | 2000 I.U./l |
| 2,4-dichlorophenyl sulphonate — sodium salt | 1 g/l |
| Monobasic potassium phosphate (KH$_2$PO$_4$) | 18 g/l |
| Sodium tetraborate (Na$_2$B$_4$O$_7$.10 H$_2$O) | 13,9 g/l |
| 4-aminophenazone | 260 mg/l |
| Aminopyrine | 15 g/l |
| Uricase (e.g. from *Aspergillus flavus*) | 100 I.U./l |

Moreover, the ratio serum/chromogen reagent is 1:40, and the spectrophotometrical dosing of the reaction product is effected at 500–520 nm.

Comparison tests have been carried out either without or with aminopyrine, observing the development of the chromogen reaction by a spectrophotometer with recorder, which has allowed to point out the interference of bilirubin on samples containing 11.6; 14.82; 15.30; 16 and 18 mg bilirubin/100 ml, respectively, since at 430 nm a peak of negative absorption is formed, due to oxidation of bilirubin by hydrogen peroxide. In fact, it has been observed that, in the presence of aminopyrine, such a peak of negative absorption is considerably reduced (65–90%).

For a better illustration of the present invention, some comparative examples are hereinafter given, from which the advantage clearly appears of using aminopyrine in the dosing of uric acid which was effected on hyperbilirubinemic samples, with Trinder's reagent added with or without aminopyrine, and the different concentration of uric acid is pointed out in both cases.

EXAMPLES

| | | Difference between the two concentrations of uric acid |
|---|---|---|
| 1. BILIRUBIN: 15.3 mg/dl | | |
| uric acid: found | 6.7 mg/dl without aminopyrine | +38,8% |
| | 9.3 mg/dl with aminopyrine | |
| 2. BILIRUBIN: 11.6 mg/dl | | |
| uric acid: found: | 6.5 mg/dl without aminopyrine | +64,6% |
| | 10.7 mg/dl with aminopyrine | |
| 3. BILIRUBIN: 16 mg/dl | | |
| uric acid: found | 7.1 mg/dl without aminopyrine | +39.4% |
| | 9.2 mg/dl with aminopyrine | |
| 4. BILIRUBIN: 14.82 mg/dl | | |
| uric acid: found | 6.5 mg/dl without aminopyrine | +41.53% |
| | 9.2 mg/dl with aminopyrine | |
| 5. BILIRUBIN: 18 mg/dl | | |
| uric acid: found | 2.0 mg/dl without aminopyrine | +55% |
| | 3.1 mg/dl with aminopyrine | |

What we claim is:

1. In a Trinder's reagent for the clinical analysis of hydrogen peroxide by the enzymatic oxidation of a metabolic substrate in the presence of bilirubin, said reagent containing 2,4-dichlorophenyl sulphonate and 4-aminophenazone; the improvement in which the Trinder's reagent contains 1 to 30 g/l of aminopyrine to block the interferring action of said bilirubin.

2. A reagent as claimed in claim 1, in which said aminopyrine is present in the amount of about 15 g/l.

3. A reagent as claimed in claim 1, containing peroxidase, about 2,000 I.U./l, 2,4-dichlorophenyl sulphonate-sodium salt about 1 g/l, monobasic potassium phosphate (KH$_2$PO$_4$) about 18 g/l, sodium tetraborate (Na$_2$B$_4$O$_7$.10 H$_2$O) about 13.9 g/l, 4-aminophenazone about 260 mg/l, aminopyrine about 15 g/l and uricase about 100 I.U./l.

* * * * *